(12) United States Patent
Eidenschink et al.

(10) Patent No.: US 6,605,056 B2
(45) Date of Patent: Aug. 12, 2003

(54) CONFORMABLE BALLOON

(75) Inventors: Tracee E. J. Eidenschink, Wayzata, MN (US); Richard C. Mattison, Zimmerman, MN (US); Christopher R. Larson, St. Paul, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/903,103

(22) Filed: Jul. 11, 2001

(65) Prior Publication Data

US 2003/0014007 A1 Jan. 16, 2003

(51) Int. Cl.7 ............................................. A61M 29/00
(52) U.S. Cl. ............................. 604/96.01; 604/101.01; 604/103.05; 606/192
(58) Field of Search .................. 604/101.01, 101.02, 604/101.05, 103, 103.07, 103.09, 103.1, 104, 171, 264, 523, 96.01, 103.01, 95.01, 103.05; 606/191, 192, 194

(56) References Cited

U.S. PATENT DOCUMENTS

| | | | |
|---|---|---|---|
| 4,423,725 A | | 1/1984 | Baran et al. ............ 128/207.15 |
| 4,763,654 A | * | 8/1988 | Jang ............................ 606/195 |
| 4,990,139 A | * | 2/1991 | Jang ........................ 604/101.01 |
| 5,049,132 A | * | 9/1991 | Shaffer et al. ......... 604/101.02 |
| 5,213,576 A | * | 5/1993 | Abiuso et al. ......... 604/103.01 |
| 5,270,086 A | | 12/1993 | Hamlin ....................... 428/35.2 |
| 5,295,962 A | * | 3/1994 | Crocker et al. ........ 604/101.02 |
| 5,320,605 A | * | 6/1994 | Sahota ................... 604/101.01 |
| 5,342,305 A | | 8/1994 | Shonk ........................ 604/101 |
| 5,419,765 A | * | 5/1995 | Weldon et al. ........... 604/99.02 |
| 5,425,709 A | * | 6/1995 | Gambale ................ 604/103.05 |
| 5,536,252 A | | 7/1996 | Imran et al. ................. 604/101 |
| 5,540,659 A | | 7/1996 | Teirstein ...................... 604/104 |
| 5,620,457 A | | 4/1997 | Pinchasik et al. ........... 606/194 |
| 5,782,740 A | | 7/1998 | Schneiderman ................ 600/1 |
| 5,827,237 A | * | 10/1998 | Macoviak et al. .......... 604/246 |
| 5,833,671 A | * | 11/1998 | Macoviak et al. .......... 604/247 |
| 5,855,546 A | | 1/1999 | Hastings et al. ................ 600/3 |
| 5,873,880 A | * | 2/1999 | Williams et al. ............ 606/108 |
| 5,980,531 A | | 11/1999 | Goodin et al. .............. 606/108 |
| 6,027,519 A | | 2/2000 | Stanford ...................... 606/198 |
| 6,048,350 A | | 4/2000 | Vrba ........................... 606/108 |
| 6,129,706 A | | 10/2000 | Janacek ........................ 604/96 |
| 6,471,672 B1 | * | 10/2002 | Brown et al. .......... 604/101.01 |
| 6,485,500 B1 | * | 11/2002 | Kokish et al. .............. 606/194 |
| 6,488,653 B1 | * | 12/2002 | Lombardo ............. 604/103.06 |
| 2002/0032406 A1 | * | 3/2002 | Kusleika ................ 604/101.02 |

FOREIGN PATENT DOCUMENTS

| | | |
|---|---|---|
| WO | 94/19049 | 9/1994 |
| WO | 96/38109 | 12/1996 |

* cited by examiner

Primary Examiner—Ira S. Lazarus
Assistant Examiner—Andrea M. Ragonese
(74) Attorney, Agent, or Firm—Vidas, Arrett & Steinkraus

(57) ABSTRACT

A medical device comprises an inner tube and an outer tube disposed about at least a portion of the inner tube. A balloon extends from the distal end of the outer tube. Within the balloon is a first expandable diaphragm, one end of which is attached to the inner tube. The first expandable diaphragm is covered by a retractable sheath disposed about the inner tube. Upon retraction of the retractable sheath, the diaphragm expands to sealingly contact the interior of the balloon in a first contact region and form at least a first compartment and a second compartment in the balloon.

23 Claims, 10 Drawing Sheets

CONFORMABLE BALLOON

BACKGROUND OF THE INVENTION

Medical balloons have been used in a number of different medical applications. One such application is balloon angioplasty in which a balloon is used to dilate a vessel. A balloon angioplasty procedure may be carried out simply by expanding a medical balloon in a vessel in order to compress plaque in a vessel.

Another such application is brachytherapy. A brachytherapy device is typically a low pressure (less than about 6 atmospheres) dilating balloon catheter that is used to center a radiation source wire in an artery. Brachytherapy devices are not commonly used to dilate an artery stenosis.

Yet another such application is balloon expansion of a prosthetic device such as a stent, graft, stent-graft and similar prosthetic devices.

As the use of balloon catheters has proliferated, there has been a proliferation in balloon catheter designs. Nevertheless, there remains a need for novel balloon catheters for use in procedures ranging from angioplasty, to brachytherapy to prosthetic expansion.

All U.S. patents and patent applications and all other published documents mentioned anywhere in this application are incorporated herein by reference in their entirety.

The invention in various of its embodiments is summarized below. Additional details of the invention and/or additional embodiments of the invention may be found in the Detailed Description of the Invention below.

BRIEF SUMMARY OF THE INVENTION

The instant invention is directed, in one embodiment, to a medical device comprising a balloon with at least one expandable diaphragm disposed therein. The device comprises an inner tube having a proximal portion and a distal portion and an outer tube disposed about at least a portion of the inner tube. The outer tube has a proximal portion and a distal portion. A balloon having a proximal end and a distal end is disposed about the inner tube. The proximal end of the balloon extends from the distal end of the outer tube. A first expandable diaphragm having a first end and a second end is attached to the inner tube at the first end, interior to the balloon. The device further comprises a retractable sheath disposed about the inner tube. The retractable sheath is retractable from a first position in which it is disposed about at least a portion of the first expandable diaphragm to a second position in which the retractable sheath is axially displaced from the first diaphragm. On retraction of the retractable sheath, the first diaphragm expands to sealingly contact the interior of the balloon in a first contact region and form at least two compartments. The device also comprises a first inflation lumen in fluid communication with the balloon. Desirably, the device will comprise at least two expandable diaphragms.

In another embodiment, the invention is directed to a balloon assembly with a variable number of compartments. The balloon assembly comprises a balloon catheter comprising an inflatable medical balloon and M expandable diaphragms disposed within the balloon where $M \geq 1$. Each diaphragm is expandable from a first position in which the diaphragm does not sealingly contact the balloon to a second position in which the diaphragm sealingly contacts the balloon. The balloon has at least M+1 compartments when the M expandable diaphragms are all in the second position. Desirably, M equals 2 or 3.

The invention is also directed to a medical balloon transformable from a first configuration to a second configuration. In the first configuration, the medical balloon has a first number of internal compartments. In the second configuration, the medical balloon has more internal compartments than in the first configuration.

In yet another embodiment, the invention is directed to a method of forming a sub-divided balloon in a bodily vessel. The method comprises the steps of providing a medical device in accordance with the instant invention, inserting at least a portion of the medical device in a bodily vessel, delivering the medical device to a desired bodily location, retracting the retractable sheath and allowing the at least one expandable diaphragm to expand so as to sealingly contact the balloon and sub-divide the balloon into compartments and inflating the balloon.

In another embodiment, the invention is directed to a medical device comprising a catheter tube, a plurality of balloon elements disposed about the catheter tube, an inflation lumen having a plurality of inflation ports therein and a movable sheath disposed about the inflation lumen. Each balloon element is disposed about at least one inflation port. The movable sheath has at least one opening therein and is movable such that each balloon element may be placed in fluid communication with the inflation lumen by moving the movable sheath to align an opening in the movable sheath with the inflation port about which the balloon element is disposed.

In another embodiment, the invention is directed to a medical device comprising a catheter tube, a balloon disposed about the catheter tube, an inflation lumen having an inflation port therein and a movable sheath disposed about the inflation lumen. The movable sheath has at least one opening therein and is movable from an open position in which the opening in the movable sheath is at least partially aligned with the inflation port to a closed position in which the opening in the sheath is displaced from the infusion port.

The invention is also directed to a medical device comprising a catheter tube, an outer medical balloon disposed about the catheter tube and a serpentine medical balloon winding about the catheter tube and disposed within the outer medical balloon. A first inflation lumen is in fluid communication with the outer medical balloon and a second inflation lumen is in fluid communication with the serpentine medical balloon. Optionally, the medical device may comprise a plurality of serpentine medical balloons disposed within the outer medical balloon and winding about the catheter tube. The serpentine medical balloons may be supplied by a single inflation lumen. The invention also allows for each serpentine medical balloon to be supplied by a separate inflation lumen.

The invention is also directed to a medical device comprising a catheter tube, an outer medical balloon disposed about the catheter tube and one or more serpentine medical balloons disposed within the outer medical balloon. Each serpentine medical balloon winds about the catheter tube. The medical device further comprises an inflation device for inflating the outer medical balloon and each of the serpentine medical balloons.

The invention is also directed in another embodiments to a method of centering a catheter tube within a medical balloon. An inventive medical device comprising a serpentine balloon winding about a catheter is provided. The serpentine balloon is disposed within an outer balloon. An inflation fluid is supplied to the outer medical balloon and to the one or more serpentine balloons to center the inner tube.

The invention is also directed a method of dilating a stenosis and treating the stenosis with radiation. The method comprises the steps of inserting at least a portion of a brachytherapy device in a bodily vessel, advancing the brachytherapy device to a desired bodily location, expanding the outer medical balloon, expanding the serpentine medical balloon and advancing the radiation source through the inner tube to the stenosis. The brachytherapy device comprises a catheter tube with an outer medical balloon disposed about the catheter tube, a serpentine medical balloon winding about the catheter tube within the outer medical balloon and a radiation source.

The invention is also directed to a medical device comprising a catheter tube, at least one spiral medical balloon wound about the catheter tube, the spiral medical balloon characterized by a pitch which may be varied and an inflation lumen in fluid communication with the spiral medical balloon. The medical device further comprises a balloon moving device which is capable of compressing the spiral medical balloon to increase the pitch of the spiral medical balloon.

A detailed description of the invention in its various embodiments is provided below.

BRIEF DESCRIPTION OF THE SEVERAL VIEWS OF THE DRAWING(S)

DETAILED DESCRIPTION OF THE INVENTION

Figure 1:
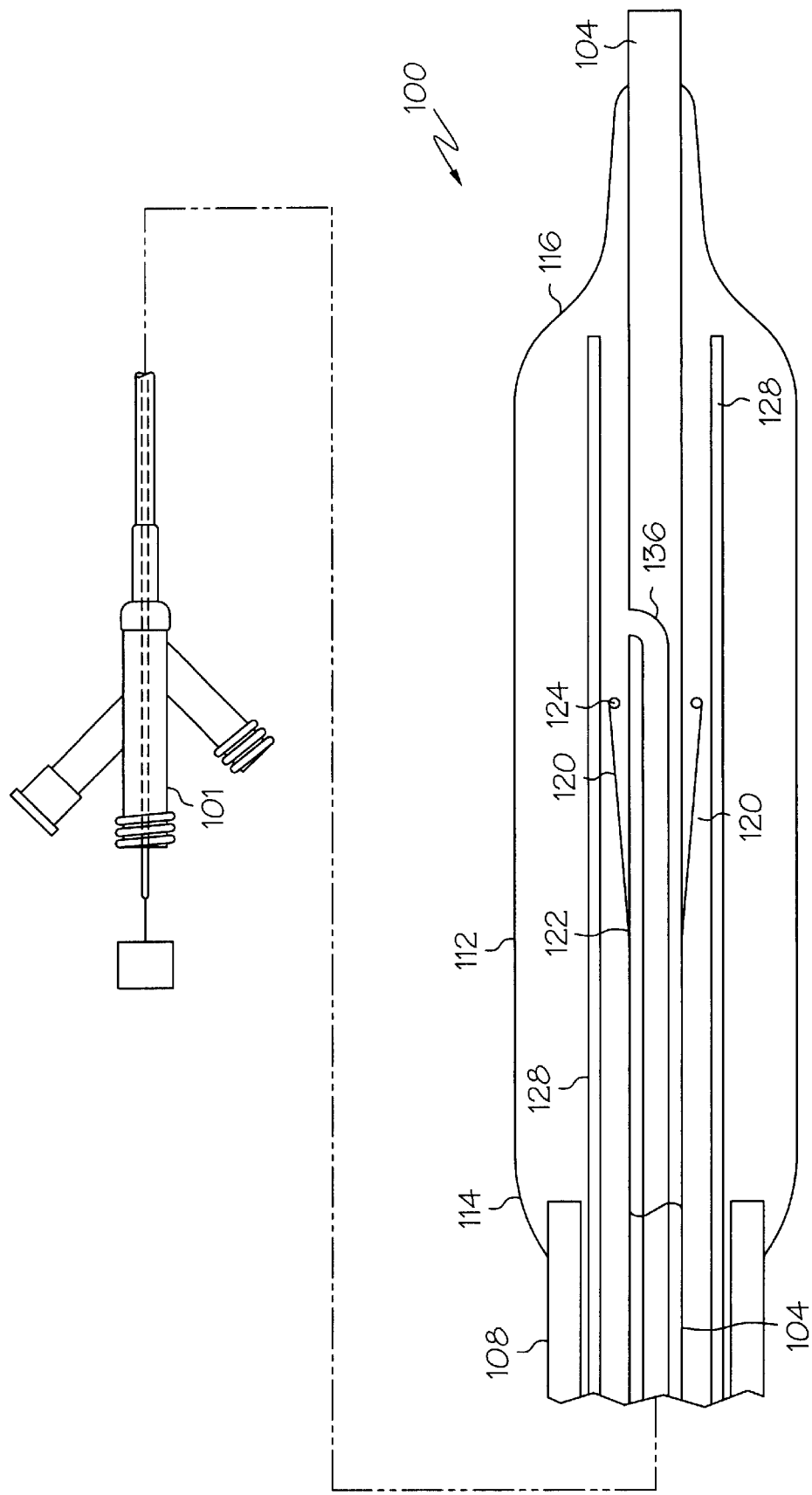
FIG. 1 shows a longitudinal cross-section of an inventive medical device with a balloon having a single compartment and an unexpanded diaphragm.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

It is noted that the presence of a manifold is shown only in FIG. 1. All of the various embodiments of the inventive medical devices discussed below may include manifolds similar or identical to that shown in FIG. 1 as well as manifolds which differ from that shown in FIG. 1.

In one embodiment, the invention is directed to a medical device having a variable number of compartments depending on the state of the balloon. As shown generally at 100 in FIG. 1, the medical device comprises manifold 101 at the proximal end of the device with an inner tube 104 and an outer tube 108 extending therefrom in a distal direction. Any suitable manifold may be used including that described in U.S. Pat. No. 5,855,546. Inner tube 104 has a proximal portion and a distal portion. An outer tube 108 having a proximal portion and a distal portion is disposed about at least a portion of inner tube 104. Inner and outer tubes 104 and 108 may be made of any suitable materials as are known in the art including polymers or combinations of polymers such as polyamide, polyester, polyimide or the like. Other suitable materials for inner tube 104 and outer tube 108 include nylons, urethanes, and polypropylene materials compatible with coatings such as silicone and/or hydrophilic coatings. In addition to hydrophilic compatible materials, any biocompatible material may be used. For example, polyethylene or polypropylene can be coated with a hydrophilic material to render them hydrophilic compatible.

Balloon 112 is disposed about a distal portion of inner tube 104. Balloon 112 has a proximal end 114 and a distal end 116. Proximal end 114 of balloon 112 extends from the distal end of outer tube 108. Balloon 112 may be made of any suitable balloon material including compliant and non-compliant materials and combinations thereof. Compliant materials include low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyether-polyamide copolymers. Suitable materials include a copolymer polyolefin material available from E. I. DuPont de Nemours and Co. (Wilmington, Del.), under the trade name Surlyn™ Ionomer and a polyether block amide available under the trade name PEBAX™. Non-compliant materials include relatively rigid of stiff high pressure polymeric materials, such as thermoplastic polymers and thermoset polymeric materials, poly(ethylene terephthalate) (commonly referred to as PET), polyimide, thermoplastic polyamide, polyamides, polyesters, polycarbonates, polyphenylene sulfides, polypropylene and rigid polyurethane. Balloon 112 may be bonded to outer tube 108 adhesively, via laser welding or via any other suitable technique.

Figure 2:
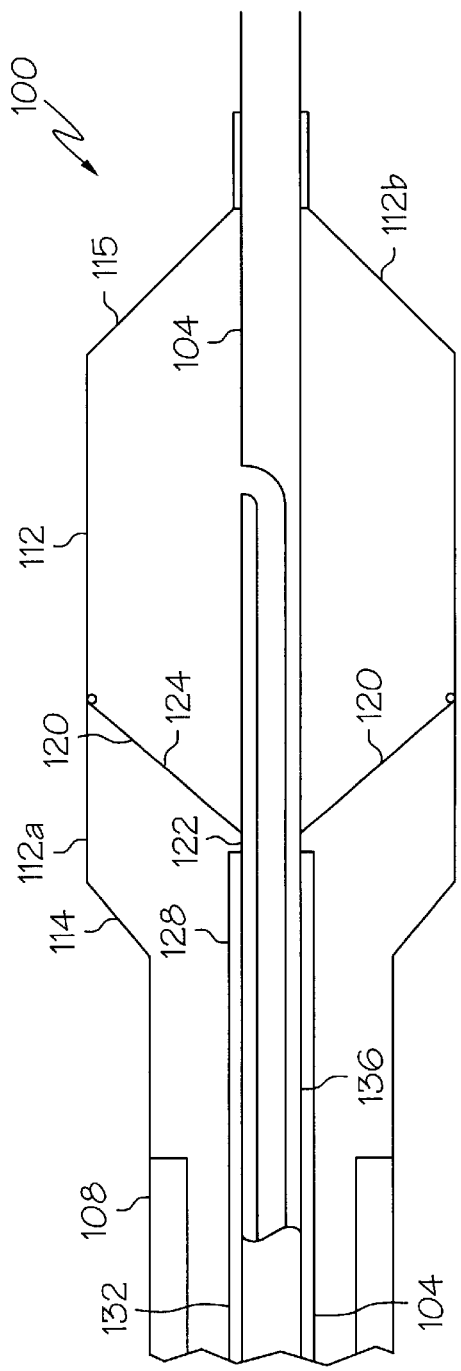
FIG. 2 shows a longitudinal cross-section of a portion of the inventive medical device of FIG. 1 with a balloon having an expanded diaphragm and two compartments.
Figure 3:
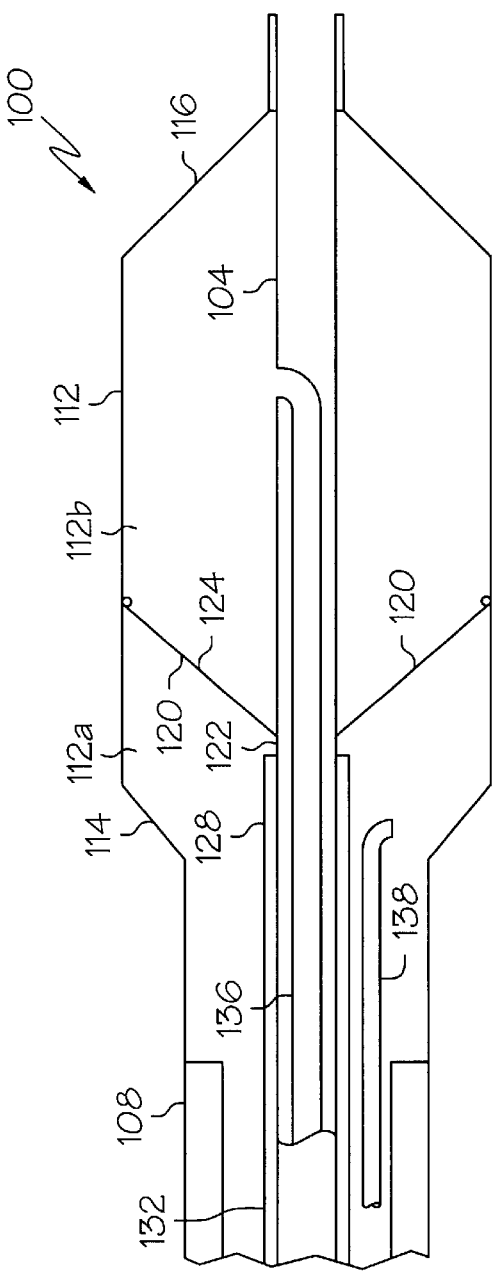
FIG. 3 shows a longitudinal cross-section of a portion of an inventive medical device similar to that of FIG. 2 with two inflation lumens.

Balloon 112 is supplied with an inflation fluid via inflation lumen 136. As shown in FIGS. 1–3, inflation lumen 136 extends in inner tube 104. Other arrangements are contemplated as well including providing an inflation lumen between outer tube 108 and inner tube 104.

A first expandable diaphragm 120 having a first end 122 attached to inner tube 104 and a second end 124 which is free is provided in the interior of balloon 112. First end 122 may be adhesively bonded, laser welded or secured via any other suitable technique. First expandable diaphragm 120 is held in place by retractable sheath 128. Retractable sheath 128 is retractable from a first position as shown in FIG. 1 to a second position as shown in FIG. 2, in which the retractable sheath is axially displaced from first expandable diaphragm 120 via the use of a retraction mechanism such as a hypotube or a pull wire (not shown).

Retractable sheath 128 may be made of any suitable material including a polyolefin such as polyethylene or polypropylene; a fluorinated polymer such as polytetrafluoroethylene or fluoroethylene propylene; a polyamide such as nylon, or other suitable material, and may be homogeneous or may be formed from more than one kind of polymer. Retractable sheath 128 should be strong enough to maintain the expandable diaphragm(s) in an unexpanded state prior to retraction of the retractable sheath.

The medical device may be constructed and arranged such that the retractable sheath retracts in a proximal direction as shown in FIGS. 1–3 or such that the retractable sheath retracts in a distal direction (not shown).

As shown in FIG. 1, balloon 112 has a single compartment. Upon expansion of first expandable diaphragm 120, as shown in FIG. 2, the first expandable diaphragm sealingly contacts balloon 112 in a first region of contact to form a balloon with two compartments 112a and 112b. Desirably, the first expandable diaphragm is not expanded until the balloon has been at least partially inflated. In the embodiment shown in FIGS. 1 and 2, once the expandable diaphragm has been expanded, the inflation lumen is only in fluid communication with second compartment 112b. Thus, upon further inflation of the balloon, a higher pressure may be attained in second compartment 112b as compared with first compartment 112a.

In another embodiment of the invention, as shown in FIG. 3, a second inflation lumen 138 is provided so that upon expansion of first expandable diaphragm 120, first compartment 112a and second compartment 112b may be independently expanded. The plurality of inflation lumens may be provided in any suitable way. For example, an inner tube such as that shown at 204 in FIG. 9d may be used.

Figure 4:
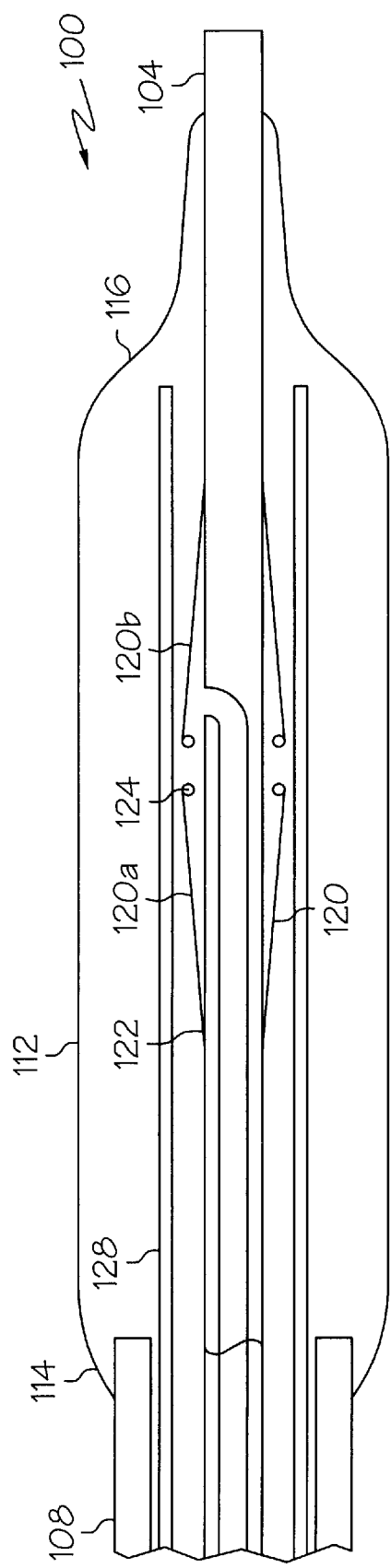
FIG. 4 shows a longitudinal cross-section of a portion of an inventive medical device having two diaphragms, each diaphragm in an unexpanded state.
Figure 5:
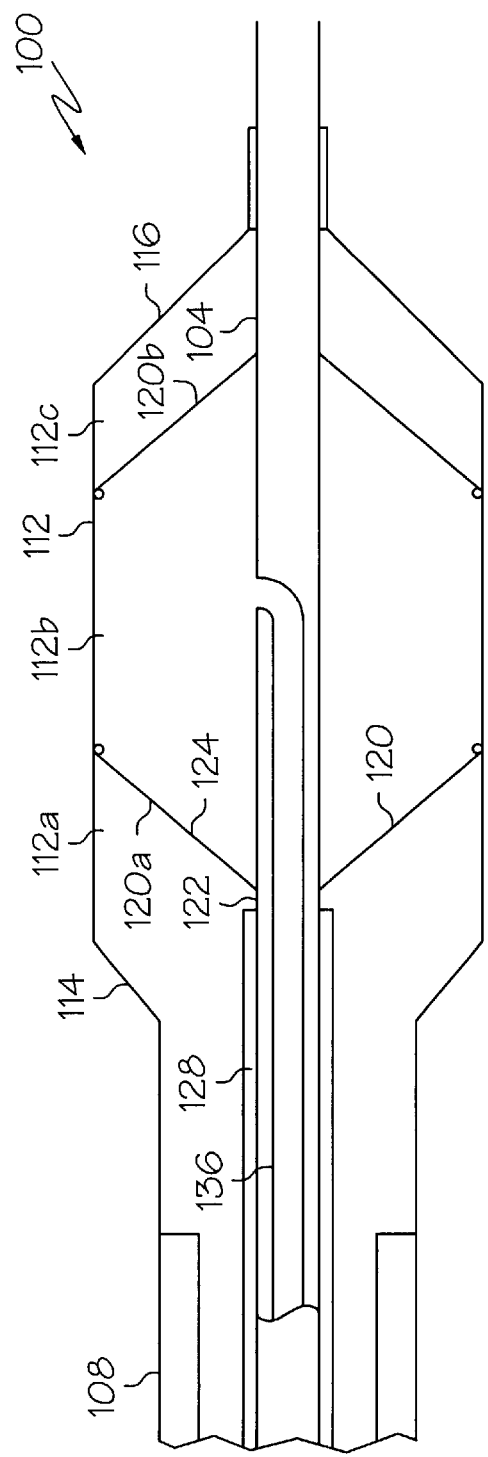
FIG. 5 shows a longitudinal cross-section of the inventive device of FIG. 4 having three compartments and one inflation lumen.

In yet another embodiment of the invention, as shown in FIGS. 4 and 5, first expandable diaphragm 120a and second expandable diaphragm 120b are provided. Both first and second expandable diaphragms in the unexpanded condition are retained by retractable sheath 128. Upon retraction of retractable sheath 128 and expansion of the first and second expandable diaphragms, the first and second expandable diaphragms sealingly contact the balloon to form first, second and third compartments 112a–c. Medical device 100 comprises a single inflation lumen 136 which is in fluid communication with the entirety of balloon 112 prior to expansion of the first and second expandable diaphragms. Subsequent to expansion of the first and second expandable diaphragms, inflation lumen 136 is in fluid communication only with compartment 112b. As such, compartment 112b can be inflated to a higher pressure than compartments 112a and 112c.

The inventive medical device of FIGS. 4 and 5 may also be constructed such that inflation lumen 136 is in fluid communication only with compartment 112a or compartment 112c subsequent to expansion of the first and second expandable diaphragms.

Figure 6:
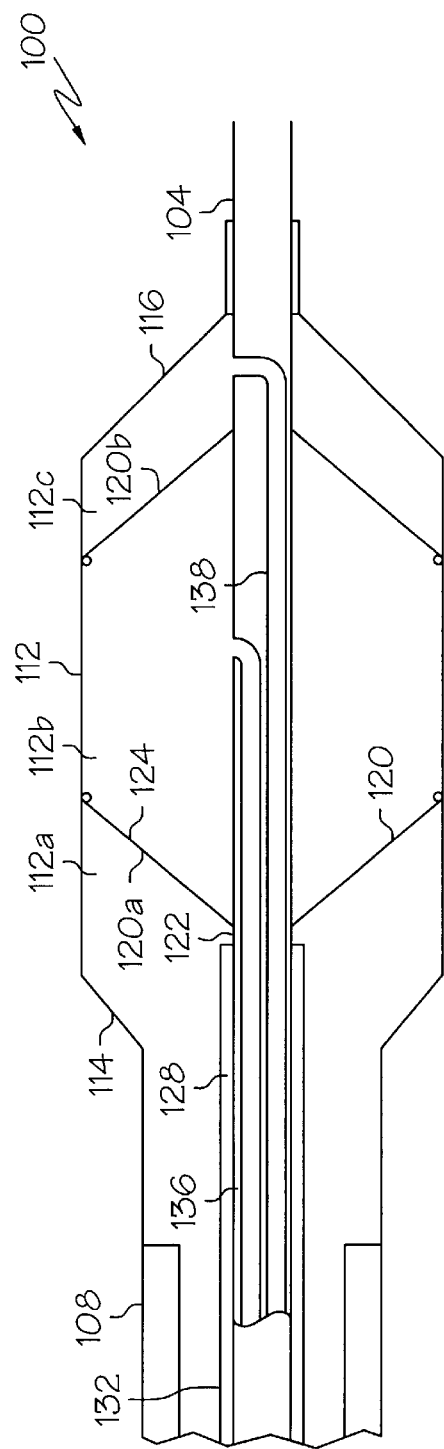
FIG. 6 shows a longitudinal cross-section of a portion of an inventive device similar to that shown in FIG. 5 having two inflation lumens.

In yet another embodiment of the invention, as shown in FIG. 6, two inflation lumens 136 and 138 are provided. Inflation lumen 136 is in fluid communication with second compartment 112b while inflation lumen 138 is in fluid communication with both compartments 112a and 112c. The medical device may also be constructed such that inflation lumen 138 is in fluid commination with either compartment 112a or compartment 112b. Any other combination of connectivities between the two inflation lumens and the three balloon compartments is also within the scope of the instant invention.

Figure 7:
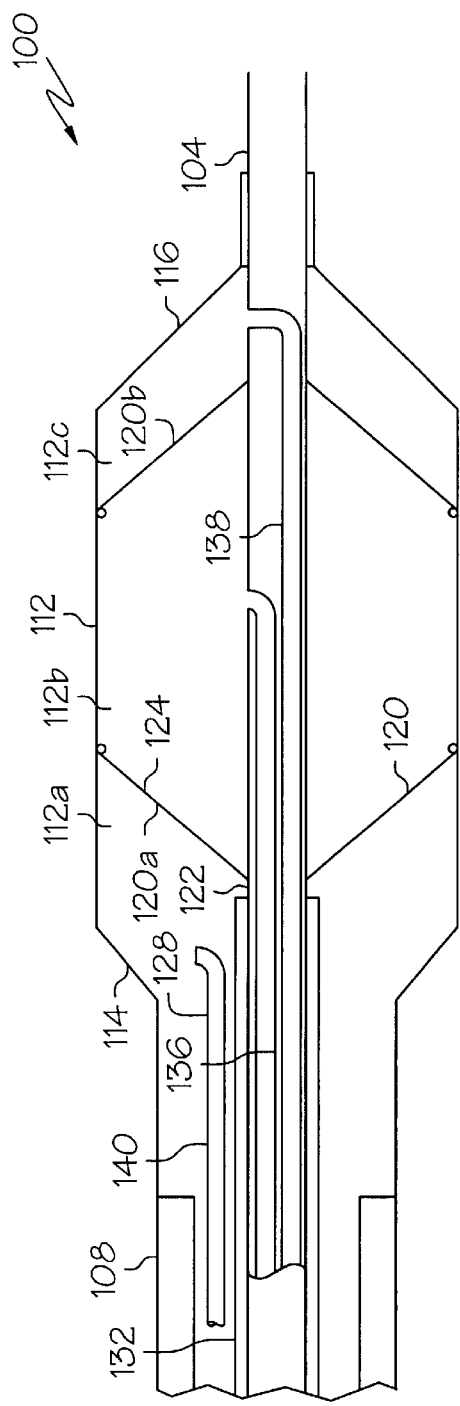
FIG. 7 shows a longitudinal cross-section of a portion of an inventive device similar to that shown in FIG. 5 having three inflation lumens.

In another embodiment of the invention, as shown in FIG. 7, three inflation lumens 136, 138 and 140 are present. Each inflation lumen is in fluid communication with a separate compartment of balloon 112.

The inventive medical devices and balloons may optionally be provided with additional expandable diaphragms and inflation lumens.

Expandable diaphragm(s) 120 may suitably be made of nylon, PEBAX, PET, Tecothane, urethane or other balloon materials. Desirably, the diaphragm will be made of a material stronger than the balloon material so that as a compartment is pressurized, the balloon will expand outward rather than the diaphragm expanding within the balloon. The length of the expandable diaphragm in the unexpanded state is desirably at least approximately equal to the maximum radius of the balloon.

In one embodiment, the expandable diaphragms are made of webs of material disposed around an umbrella-like frame. The umbrella-like frame may comprise one or more ribs made of a stiff polymer, stainless steel, nitinol or the like. Webs of material may be disposed about the ribs by dipping the ribs in a polymeric material or by blow molding a polymeric material onto the ribs. Other suitable techniques include securing the material to the ribs via the use of adhesives or laser welding the material to the ribs. The expandable diaphragms should be constructed and arranged such that when the balloon is pressurized, the diaphragm is forced outward to contact and form a seal with the interior of the balloon wall.

The inventive medical device may be provided in the form of a stent delivery catheter with a stent disposed about the balloon. Such a device, with a balloon which may be formed into a plurality of compartments inflatable to different pressures, allows for the differential expansion of various portions of the stent. It may be desirable, for example, to apply a greater pressure to a center portion of a stent than to the ends. A catheter having a balloon such as those shown in FIGS. 4–6 may be suitable for such a purpose with greater pressure supplied to the middle compartment 112b than to the proximal and distal compartments 112a and 112c.

The invention is also directed to a balloon assembly with a variable number of compartments. The balloon assembly comprises an inflatable balloon and M expandable diaphragms disposed within the balloon where M≧1. Each diaphragm is expandable from a first position in which the diaphragm does not sealingly contact the interior of the balloon wall to a second position in which the diaphragm sealingly contacts the interior of the balloon wall. The balloon has at least M+1 compartments when the M expandable diaphragms are all in the second position.

The balloon assembly may comprise an inner tube disposed within the balloon and a retractable sheath which is retractable from a first position to a second position. In the first position, the retractable sheath is disposed about the inner tube and the expandable diaphragms. In the second position, the retractable sheath is axially displaced from the expandable diaphragm to allow the expandable diaphragms to open and sealingly contact the balloon and form M+1 compartments. The balloon assemblies shown in FIGS. 1–6 have two and three compartments, respectively.

The invention is also directed to medical balloons such as those shown by way of example in FIGS. 1–6 which are transformable from a first configuration to a second configuration. As shown in FIG. 1, medical balloon 112 in the first configuration has a single internal compartment 112. As shown in FIG. 2, medical balloon 112 in the second configuration has two internal compartments 112a and 112b. More generally, the inventive balloon have a first number of compartments in the first configuration and a second number of compartments in the second configuration in excess of the number of compartments in the first configuration.

The instant invention is also directed to a method of forming a sub-divided balloon in a bodily vessel. In accordance with the method, a medical device as disclosed herein is provided. At least a portion of the medical device is inserted in a bodily vessel and delivered to a desired bodily location. The retractable sheath is retracted and the at least one expandable diaphragm is allowed to expand so as to sealingly contact the balloon and sub-divide the balloon into compartments. During the practice of the method, the balloon is inflated. Desirably, the balloon is at least partially inflated prior to the retracting step. The balloon may be further inflated following deployment of the expandable diaphragm(s).

In accordance with the inventive method, the balloon is subdivided into at least two compartments. Desirably, the at least two compartments are inflated to different pressures.

The invention also contemplates subdividing the balloon into three or more compartments. Each of the compartments may be inflated to a different pressure or several of the compartments may be inflated to the same pressure.

Figure 8:
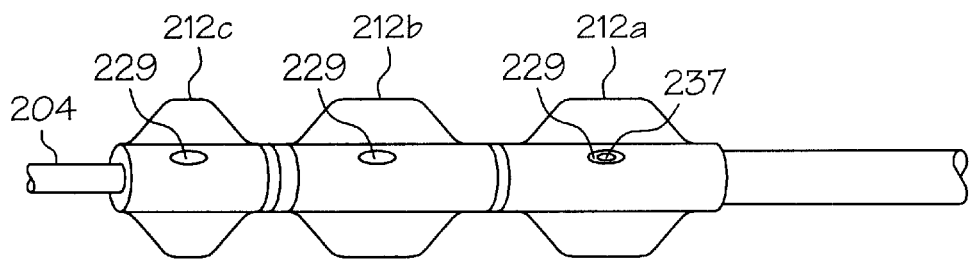
FIG. 8 is a perspective view with parts cut away of a segmented balloon with an inflation lumen and sheath.
Figure 9A:
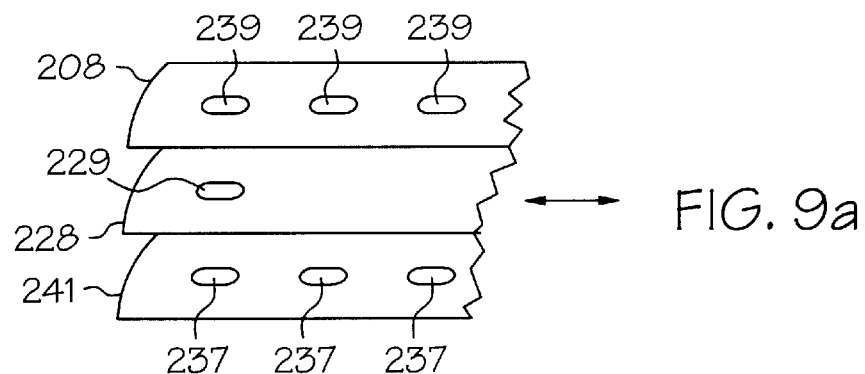
FIG. 9a is a fragmentary view of the inflation lumen, sheath and outer tube of FIG. 8.

In yet another embodiment, as shown in FIGS. 8 and 9a, the invention is directed to a medical device comprising a catheter tube 204 and a plurality of balloon elements 212a–c disposed about inner catheter tube 204 and outer catheter tube 208. Catheter tube 204 has an inflation lumen 241 running therein with a plurality of inflation ports 237 therein. Each balloon element 212 is disposed about at least one inflation port 237. Movable sheath 228 is disposed between catheter tube 204 and outer tube 208 has at least one opening 229 therein. As shown in FIG. 9a, movable sheath 228 is movable axially. By moving sheath 228 and aligning opening 229 in sheath 228, an inflation port 237 and an opening 229 in outer tube 208, a given balloon element 212 may be placed in fluid communication with the inflation lumen extending in catheter tube 204.

The medical device of FIG. 8 has three balloon elements. The invention, more generally, contemplates providing at least two balloon elements. Embodiments having four, five, six or more balloon segments are contemplated as well. Each balloon element may be disposed about a single inflation port or about a plurality of inflation ports.

The inventive medical device as shown in FIGS. 8 and 9a is formed by providing a plurality of separate balloons. The inventive medical device may also be formed from a single balloon which has been bonded to the catheter tube in a plurality of locations axially displaced from one another along a portion of the catheter tube.

In one embodiment of the invention, adjacent balloon elements are independently inflatable. In another embodiment, the openings in the sheath and catheter tube may be provided such that no more than one balloon element at a time can be in fluid communication with the inflation lumen. The sheath may be provided with one opening therein. The invention also contemplates the use of a movable sheath with a plurality of openings therein.

Figure 9B:
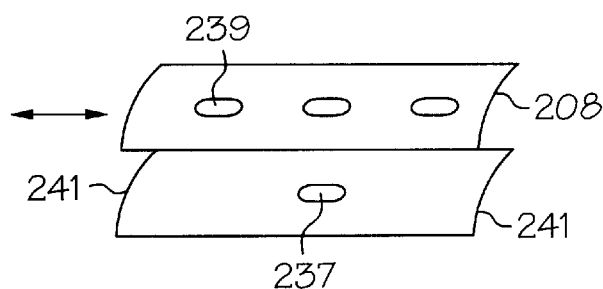
FIGS. 9b and 9c are fragmentary views of inflation lumens and outer tubes which may be moved relative to one another to allow for sequential inflation of a plurality of balloon using a single inflation lumen.

The medical device of FIG. 8 may also be provided in an embodiment in which the sheath of FIG. 9a is absent. As shown in FIG. 9b, inflation lumen 241 has one or more inflation ports 237 therein and outer tube 208 has a plurality of openings 239 therein. Outer tube 208 may be moved in an axial direction relative to inner tube 204 to align the inflation port in the inflation lumen and one of the openings in outer tube 208, thus allowing for selective inflation of one of the balloons 212.

Figure 9C:
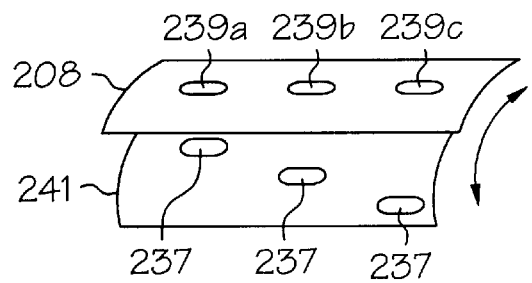

In the embodiment of FIG. 9c, inflation lumen 237 comprises a plurality of axially and circumferentially offset inflation ports 237. When at least one of outer tube 208 and inflation lumen 241 is rotated relative to the other, each of openings 239a–c will come into and out of alignment with one of inflation ports 237 to allow balloons 212a–c to be inflated in sequence.

Figure 9D:
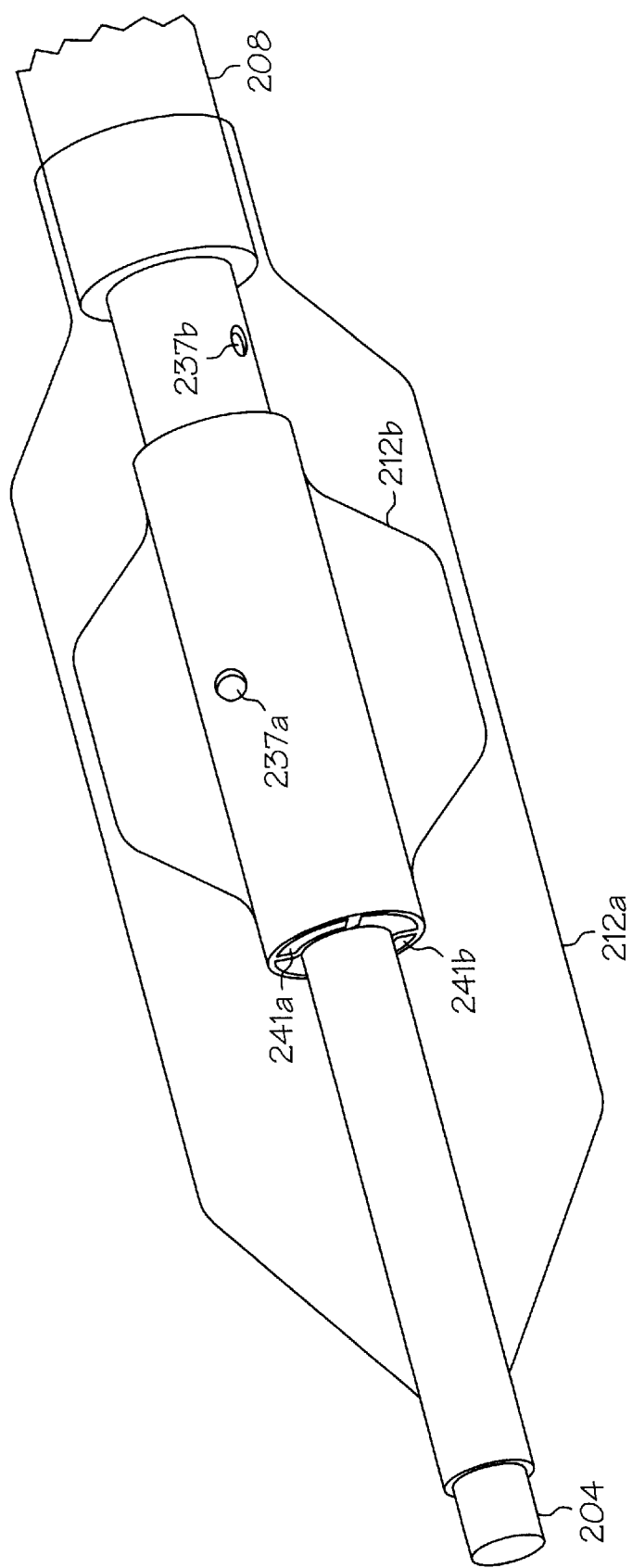
FIG. 9d is a fragmentary view of a catheter having two balloons.

In another the embodiment, as shown in FIG. 9d, a plurality of inflation lumens 241a and 241b extend in inner tube 204. Inner tube 204 extends from the distal end of outer catheter tube 208. First balloon 212a extends from the distal end of outer tube 208 to the distal end of inner tube 204. First inflation lumen 241a opens into outer balloon 212a via inflation port 237a. Second inflation lumen 241b opens into outer balloon 212b via inflation port 237b.

Figure 10:
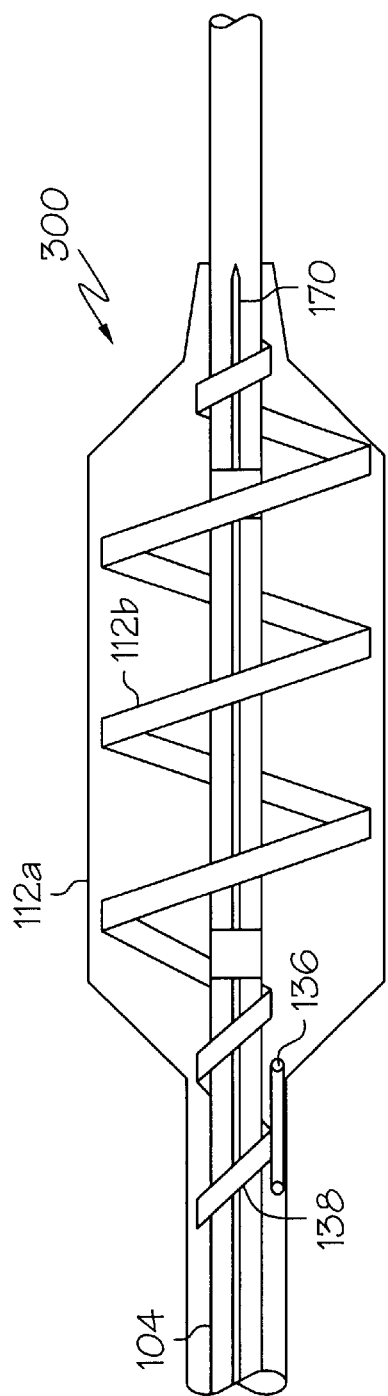
FIG. 10 is a longitudinal cross-section of a portion of an inventive catheter having a spiral balloon and two inflation lumens.

The invention is also directed to a medical device such as that shown generally at 300 in FIG. 10. Medical device 300 comprises inner tube 104, outer tube 108 and outer medical balloon 112a disposed about a distal portion of the outer tube 108. Medical device 300 further comprises a spiral medical balloon 112b disposed about inner tube 104 and within outer medical balloon 112a.

Desirably, spiral medical balloon 112b extends at least one complete turn (360°) about the inner tube. Balloons extending two (720°), three (1080°) or more turns about the catheter tube are also contemplated. The balloon may also extend a non-integral number of complete turns about the inner tube. For example, a spiral balloon for use in the instant invention may make one and a half turns around the inner tube. The exact number of turns will depend on a variety of factors including the width of the balloon, the length of the inner tube over which the spiral balloon is wound and the length of the outer balloon.

More generally, the invention contemplates providing a serpentine balloon about the inner tube and within the outer balloon. The serpentine balloon may be wound in a single direction about the inner tube or may double back on itself.

Figure 11:
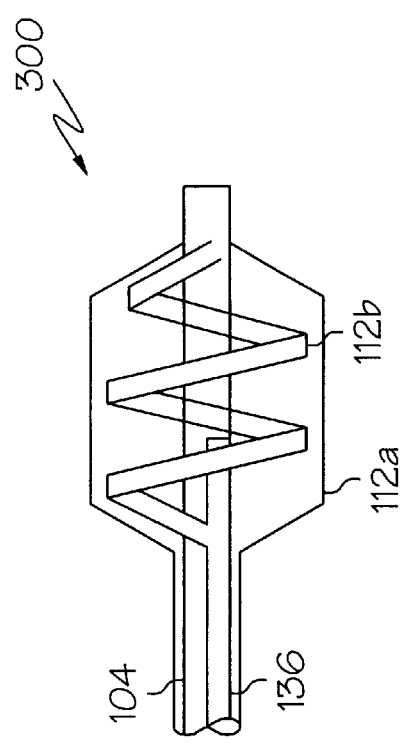
FIG. 11 is a longitudinal cross-section of a portion of an inventive catheter having a spiral balloon and a single inflation lumen.

As shown in FIG. 10, first inflation lumen 136 is in fluid communication with outer medical balloon 112a and second inflation lumen 138 is in fluid communication with spiral medical balloon 112b. The invention is also directed to embodiments having only a single inflation lumen 136 in fluid communication with outer medical balloon 112a and spiral medical balloon 112b, as shown in FIG. 11. Single inflation lumen 136 may be constructed and arranged to inflate outer medical balloon 112a and spiral medical balloon 112b in a manner similar to that disclosed above using an inflation lumen with a movable sheath disposed thereabout, as is illustrated, by way of example, in FIG. 9a.

Figure 12:
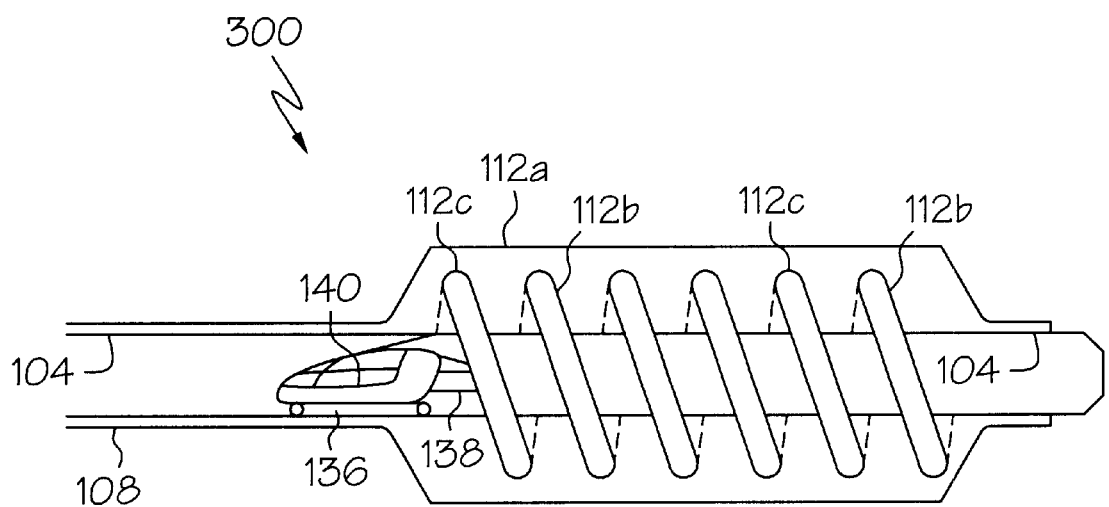
FIG. 12 is a fragmentary side view of the distal end of an inventive catheter having a plurality of spiral balloons.

An example of an inventive medical balloon comprising a plurality of spiral balloons within an outer balloon is shown in general at 300 in FIG. 12. Medical device 300 comprises inner tube 104, outer tube 108 and outer medical balloon 112a disposed about a distal portion of the outer tube 108. Medical device 300 further comprises a plurality of spiral medical balloons disposed about inner tube 104 including first spiral balloon 112b and second spiral balloon 112c. Outer medical balloon 112a is in fluid communication with a first inflation lumen 136. First spiral balloon 112b is in fluid communication with second inflation lumen 138 and second spiral balloon is in fluid communication with third inflation lumen 140. Optionally, the second spiral balloon may be made of a material capable of withstanding higher pressure than the first spiral balloon.

The first and second spiral balloons may be simultaneous inflated or sequentially inflated. Desirably, one of the spiral balloons will be inflated to a first pressure and the other spiral balloon will be inflated to a second, higher pressure. The combination of high and low pressure spiral balloons allows for greater flexibility of the balloon, permitting the balloon to better conform to the vessel in which it is located.

Where a plurality of spiral medical balloons are provided, each spiral medical balloon may be in fluid communication with a separate inflation lumen or may be supplied from the same inflation lumen. Depending on the design, some or all of the balloons may be independently inflated or simultaneously inflated.

Figure 13:
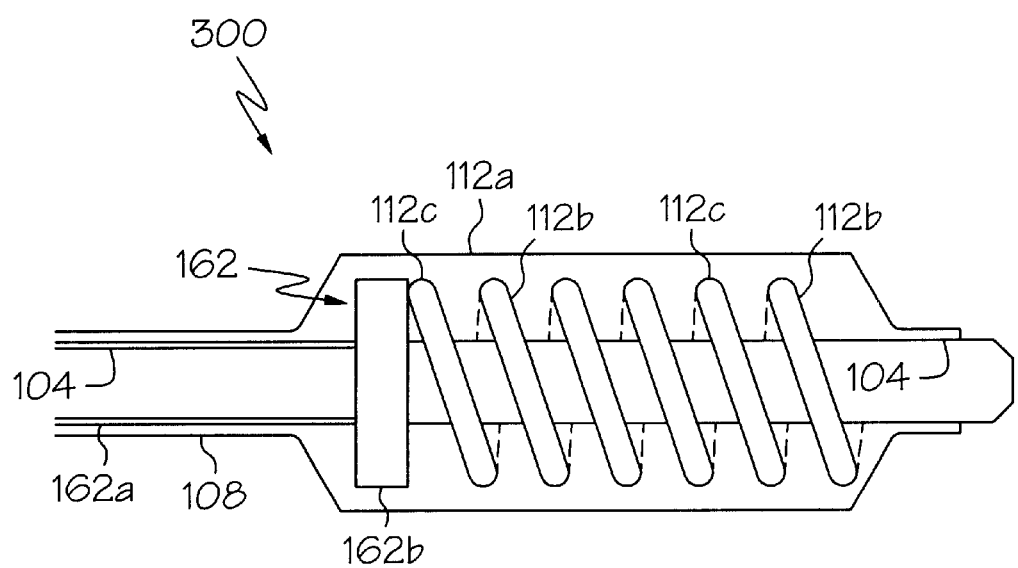
FIG. 13 is a longitudinal cross-section of a portion of an inventive catheter having a spiral balloon whose pitch may be altered.

The inventive medical devices comprising spiral balloon disclosed herein may further comprise a movable collar for altering the pitch or density of the coils of the spiral balloon. As shown generally at 300 in FIG. 13, medical device 300 comprises inner tube 104, outer tube 108 and optional outer medical balloon 112a disposed about a distal portion of the outer tube 108. Medical device 300 further comprises spiral balloon 112b and spiral balloon 112c disposed about inner tube 104. Typically, at least one spiral balloon is present. Optional outer medical balloon 112a is in fluid communication with a first inflation lumen (not shown). First spiral balloon 112b is in fluid communication with a second inflation lumen (not shown) and optional second spiral balloon 112c is in fluid communication with a third inflation lumen (not shown). Balloon moving device 162, in the form of a pushing device, is adjacent to spiral balloon 112c and may be moved in a distal direction to increase the pitch of the coils of spiral balloon 112c and spiral balloon 112b. The balloon moving device, shown generally at 162, may be in the form of a movable catheter tube 162a, optionally having a collar 162b at a distal end thereof as shown in FIG. 13. The balloon moving device may also be in the form of a movable collar extending from a push rod. Spiral balloons 112b and 112c are shown in FIG. 14 after being pushed in a distal direction by pushing device 162.

Typically, the balloon moving device is moved in a distal direction to increase the pitch of the spiral balloon. It is also within the scope of the invention to provide a balloon moving device which operates to increase the pitch of the spiral balloon by pushing the spiral balloon in a proximal direction. Such a device is shown generally at 300 in FIG. 15. Distal collar 162b, coupled to a movable catheter tube or a pull rod or wire 162a, increases the pitch of spiral balloons 112b and 112c when it is moved in a proximal direction. Optionally, proximal collar 164 may be provided to prevent spiral balloon 112b from being pushed too far in a proximal direction.

Figure 14:
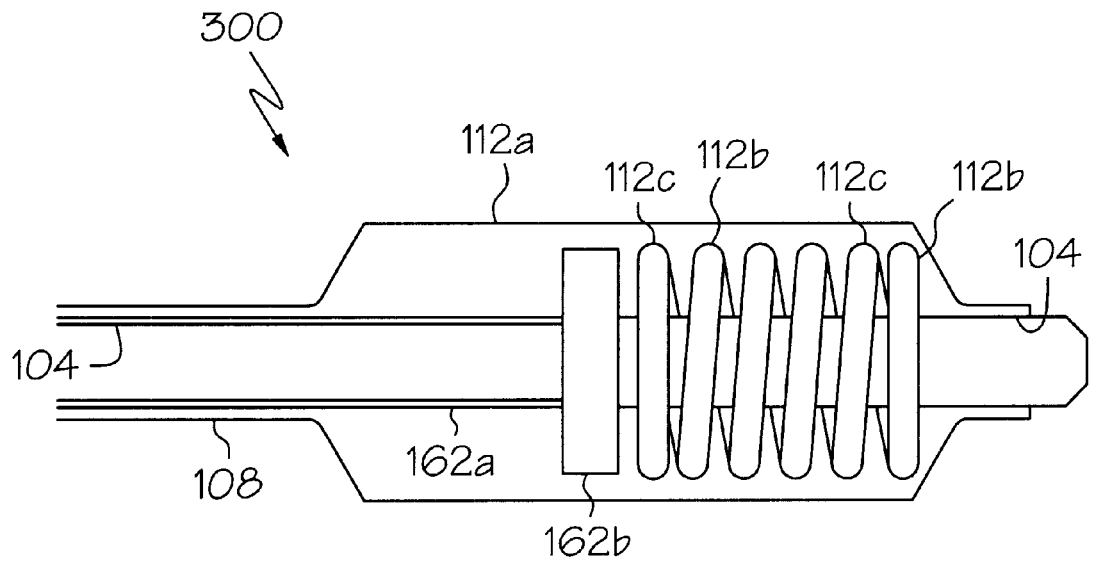
FIG. 14 is a longitudinal cross-section of the inventive device of FIG. 13 after the pitch of the spiral balloon has been increased.
Figure 15:
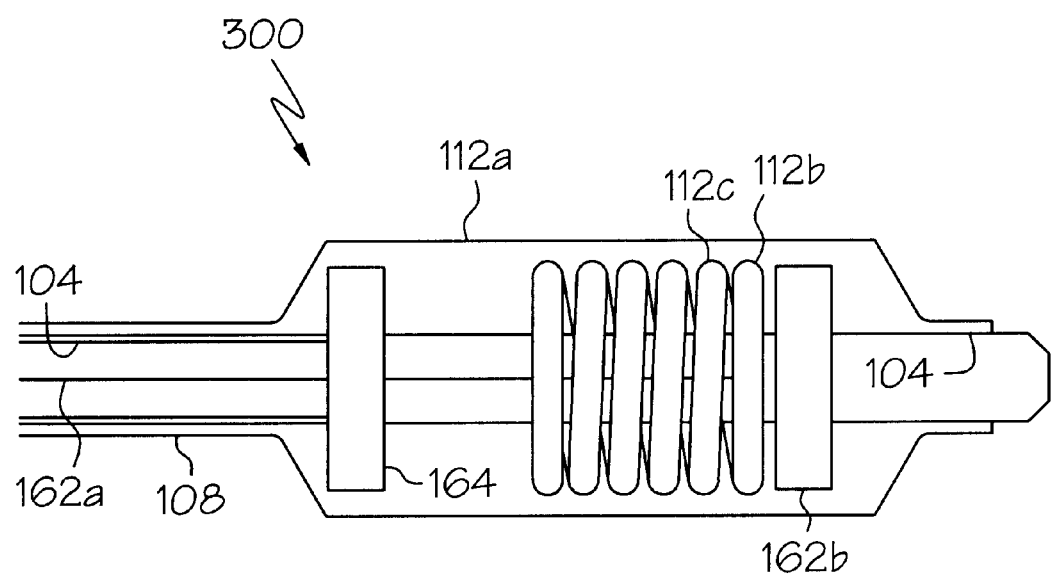
FIG. 15 is a longitudinal cross-section of a portion of another inventive catheter having a spiral balloon whose pitch may be altered.

In the embodiment of FIGS. 13–15, outer balloon 112a is typically inflated to a lower pressure than spiral balloons 112b and 112c. The invention is also directed to embodiments having one or more spiral balloons with a variable pitch but lacking an outer balloon.

Figure 16:
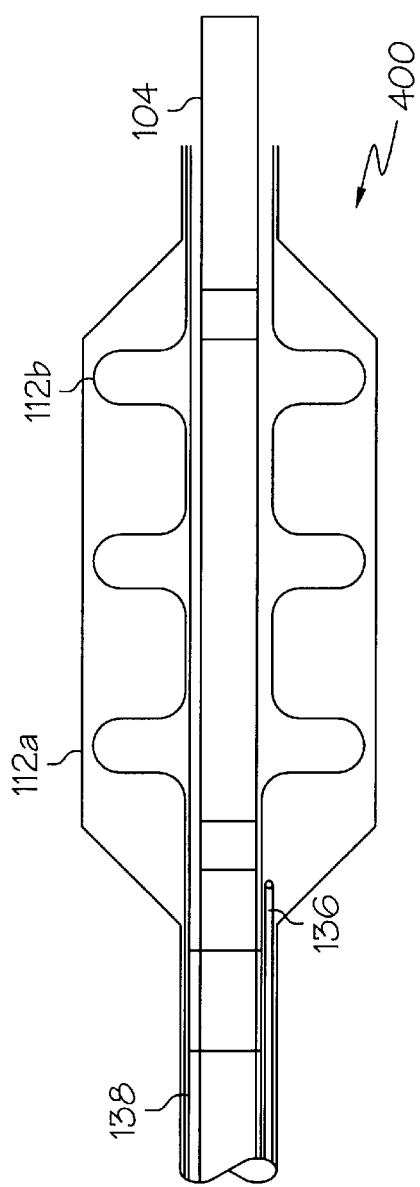
FIG. 16 is a longitudinal cross-section of a portion of an inventive catheter having a segmented balloon.

The invention is further directed to a medical device such as that shown generally at 400 in FIG. 16. Medical device 400 includes an inner tube 104, an outer balloon 112a and a segmented inner balloon 112b. Inflation lumen 136 is in fluid communication with outer balloon 112a while inflation lumen 138 is in fluid communication with segmented balloon 112b. All of the segments are inflated simultaneously via the one inflation lumen 136. The invention also contemplates providing each of the segments of segmented balloon 112b with a separate inflation lumen so that each segment may be inflated independently of the other segments. The invention further contemplates using the single lumen and sheath arrangement disclosed above to inflate one or more segments at a time depending on the construction of the sheath and inflation lumen.

The inventive balloon catheter may be used for a number of purposes where centering is important. One such purpose is as part of a brachytherapy device. Desirably, when used as a brachytherapy device, the inventive balloon comprises an outer medical balloon made of a high pressure resistant material such as DynaLeap II balloon material (Boston Scientific), Pebax, nylon, non-compliant and hinged compliant materials and a spiral balloon made of a material such as polyethylene, soft nylon, soft pebax, polyolefin coploymer, or other standard balloon materials. Desirably, the combination of balloons will have a rated balloon pressure of at least 10 atmospheres. By employing such a combination of balloons, the inventive medical device may be used to dilate a stenosis and treat the stenosis with radiation without having to remove the dilation catheter for a radiation delivery catheter. This lowers the likelihood of source misplacement and edge effects.

When used as a brachytherapy device, the medical device shown in FIGS. 10–16 may further comprise a radioactive wire 170 as shown by way of example in FIG. 10. The balloons described herein aid in maintaining the inner tube or other lumen containing the radioactive source centered in the vessel even around turns and curves in the vasculature.

In practice, an inventive medical device such as those shown in FIGS. 10–16 may be used to deliver radiation to a desired bodily location by inserting the distal end of the device in the vasculature and advancing it to a desired bodily location. The catheter may be directed to the location with or without the use of a guidewire. Once at the desired bodily location, outer balloon 112a may be inflated to dilate the treatment site. Balloon 112a may optionally be inflated via the use of an inflation gas such as nitrogen, carbon dioxide or other non-toxic gas to minimize absorption of radiation by the inflation fluid. Inner balloon 112b may then be inflated to center the catheter in the vasculature. The radioactive wire may then be delivered through the catheter to the desired bodily location to treat the vessel.

For additional details concerning brachytherapy catheters may be found in U.S. Pat. No. 5,855,546, the contents of which is incorporated herein by reference. The inventive brachytherapy catheters disclosed herein may employ the combination of inner and outer balloons disclosed herein in combination with the brachytherapy catheters described in U.S. Pat. No. 5,855,546 suitably modified to accommodate two inflation lumens or to allow for the inflation of multiple balloons.

Figure 17:
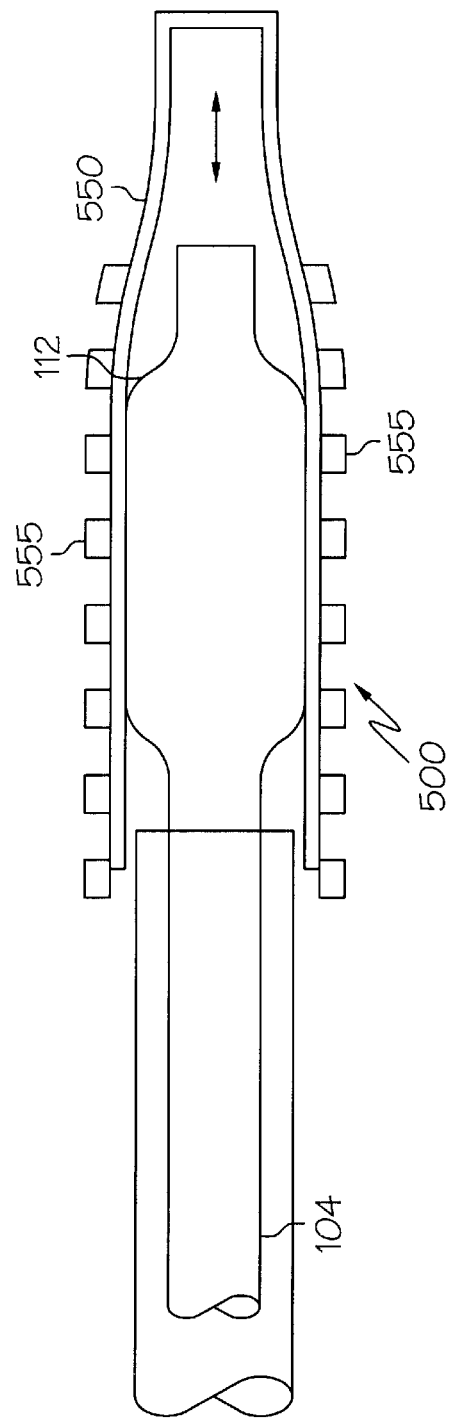
FIG. 17 is longitudinal cross-section of a portion of an inventive catheter having a movable balloon.

In yet another embodiment, as shown in FIG. 17, the invention is directed to a stent delivery catheter, shown generally at 500, comprising a balloon 112 disposed about inner tube 104 and an elastomeric sheath 550. Stent 555 is disposed about elastomeric sheath 550. Balloon 112 is shorter than stent 555. Balloon 112 is movable relative to elastomeric sheath 550 and stent 555. Stent 555 may be deployed gradually by incrementally moving the balloon under the elastomeric sheath, inflating the balloon to expand a portion of the stent and repeating the process until the entirety of the stent has been expanded. The balloon may be deflated and reinflated as it moves under the elastomeric sheath or may be moved under the stent in the fully expanded state.

The invention is also directed to novel methods of implanting a stent in a bodily vessel. The methods involve introducing the distal end of an inventive stent delivery catheter in a bodily vessel and advancing the distal end to a site to be treated. The balloon is then inflated under a portion of the stent to expand a portion of the stent. The balloon is then deflated and moved under another portion of the stent to expand the next portion of the stent and the process repeated until the entirety of the stent is expanded.

The inventive medical devices described herein may be provided in a variety of forms including rapid exchange, fixed wire and over-the-wire embodiments as are known in the art. A more detailed discussion of these forms of catheter may be found in U.S. Pat. No. 5,855,546 as well as other catheter-related patents.

The inventive medical devices may be used as a variable angioplasty catheter or as a stent delivery catheter. It is noted that the term 'stent' is intended to refer to stents, grafts, stent-grafts, vena cava filters and other expandable prostheses for insertion in the body.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1; claim 4 may be taken as alternatively dependent on claim 3 or claim 1, claim 5 may be taken as alternatively dependent from claim 3 or claim 1; etc.).

What is claimed is:

1. A medical device comprising:
    an inner tube having a proximal portion and a distal portion;
    an outer tube disposed about at least a portion of the inner tube, the outer tube having a proximal portion and a distal portion;
    a balloon disposed about the inner tube, the balloon having a proximal end and a distal end, the proximal end of the balloon extending from the distal end of the outer tube;
    a first inflation lumen in fluid communication with the balloon;
    at least one first expandable diaphragm having a first end and a second end, the first end attached to the inner tube, the at least one first expandable diaphragm interior to the balloon;
    a retractable sheath disposed inside of the balloon about the inner tube, the retractable sheath retractable from a first position in which it is disposed about at least a portion of the at least one first expandable diaphragm to a second position in which the retractable sheath is axially displaced from the at least one first expandable diaphragm.

2. The medical device of claim 1 wherein the first diaphragm is constructed and arranged so that on refraction of the retractable sheath, the diaphragm expands to sealingly contact the interior of the balloon in a first contact region and form at least a first compartment and a second compartment in the balloon.

3. The medical device of claim 2 wherein the retractable sheath in the first position is disposed about the entirety of the first expandable diaphragm.

4. The medical device of claim 2 further comprising a second inflation lumen in fluid communication with the balloon, the first inflation lumen in fluid communication with the first compartment and the second inflation lumen in fluid communication with the second compartment on expansion of the diaphragm.

5. The medical device of claim 2 further comprising a second expandable diaphragm interior to the balloon, the second expandable diaphragm having a first end and a second end, the first end attached to the inner tube, the retractable sheath disposed about at least a portion of the second expandable diaphragm, the second diaphragm expanding to sealingly contact the interior of the balloon in a second contact region on retraction of the retractable sheath to form a third compartment in the balloon.

6. The medical device of claim 5 wherein the retractable sheath in the first portion is disposed about the entirety of the second expandable diaphragm.

7. The medical device of claim 5 further comprising three inflation lumens wherein each balloon compartment is in fluid communication with an inflation lumen on expansion of the first and second diaphragms.

8. The medical device of claim 2 further comprising a stent disposed about at least a portion of the balloon.

9. The medical device of claim 5 further comprising a stent disposed about at least a portion of the balloon.

10. A method of forming a sub-divided balloon in a bodily vessel comprising the steps of:

providing a medical device as in claim 1;

inserting at least a portion of the medical device in a bodily vessel;

delivering the medical device to a desired bodily location;

retracting the retractable sheath and allowing the at least one first expandable diaphragm to expand so as to sealingly contact the balloon and sub-divide the balloon into compartments and inflating the balloon.

11. The method of 10 wherein the balloon is at least partially inflated prior to the retracting step.

12. The method of claim 11 wherein the balloon is subdivided into at least 2 compartments.

13. The method of claim 11 wherein following inflation of the balloon, the at least 2 compartments are inflated to different pressures.

14. The method of claim 10 wherein the balloon is subdivided into at least 3 compartments.

15. A medical device comprising:

a catheter tube;

a plurality of balloon elements disposed about the catheter tube;

an inflation lumen having a plurality of inflation ports therein, each balloon element disposed about at least one inflation port;

a movable sheath disposed about the inflation lumen, the movable sheath having a plurality of openings therein, the movable sheath movable such that each balloon element may be placed in fluid communication with the inflation lumen by moving the movable sheath to align an opening in the movable sheath with the inflation port about which the balloon element is disposed.

16. The medical device of claim 15 comprising at least three balloon elements.

17. The medical device of claim 16 wherein the balloon elements are formed from a single balloon which has been bonded to the catheter tube in a plurality of locations axially displaced from one another along a portion of the catheter tube.

18. The medical device of claim 16 wherein adjacent balloon elements are independently inflatable.

19. The medical device of claim 16 wherein the plurality of openings in the sheath and the inflation ports are arranged such that no more than one balloon element at a time can be in fluid communication with the inflation lumen.

20. The medical device of claim 15 wherein each balloon element is disposed about a single inflation port.

21. The medical device of claim 15 wherein the inflation lumen forms a part of the catheter tube.

22. A medical device comprising:

a catheter tube;

a balloon disposed about the catheter tube;

an inflation lumen having a plurality of inflation ports therein; and a movable sheath disposed about the inflation lumen, the movable sheath having at least one opening therein, the movable sheath movable from an open position in which the opening in the movable sheath is at least partially aligned with the plurality of inflation ports to a closed position in which the opening in the sheath is displaced from the inflation ports.

23. The medical device of claim 22 wherein the inflation lumen forms a part of the catheter tube.

* * * * *